United States Patent [19]

Koepke et al.

[11] Patent Number: 4,847,018

[45] Date of Patent: Jul. 11, 1989

[54] PROCESS FOR PRODUCING PETROLEUM SULFONATES

[75] Inventors: Jeffery W. Koepke, La Habra; Wen-Ching Hsieh, Yorba Linda; June M. Bostich, Brea, all of Calif.

[73] Assignee: Union Oil Company of California, Los Angeles, Calif.

[21] Appl. No.: 185,286

[22] Filed: Apr. 15, 1988

Related U.S. Application Data

[63] Continuation of Ser. No. 912,072, Sep. 25, 1986, abandoned, which is a continuation-in-part of Ser. No. 371,992, Apr. 26, 1982, abandoned.

[51] Int. Cl.$^4$ ............................................. C07C 143/24
[52] U.S. Cl. ...................................................... 562/33
[58] Field of Search ............ 260/513 T, 504 S, 505 S, 260/505 R

[56] References Cited

U.S. PATENT DOCUMENTS

| | | | |
|---|---|---|---|
| 2,205,924 | 6/1940 | Frame | 260/504 |
| 2,815,370 | 12/1957 | Hutchings et al. | 260/504 |
| 2,857,426 | 10/1958 | Hutchings et al. | 260/504 |
| 2,909,563 | 10/1959 | Whitney | 260/504 |
| 3,302,713 | 2/1967 | Ahearn et al. | 166/9 |
| 3,373,808 | 3/1968 | Patton | 166/9 |
| 3,956,372 | 5/1976 | Coleman et al. | 260/505 S |
| 4,144,266 | 3/1979 | Plummer et al. | 260/505 S |
| 4,226,805 | 10/1980 | Bauer | 260/505 R |
| 4,240,978 | 12/1980 | Berg | 260/505 P |
| 4,446,036 | 5/1984 | Hsieh et al. | |

*Primary Examiner*—Alan Siegel
*Attorney, Agent, or Firm*—Alan H. Thompson; Gregory F. Wirzbicki; June M. Bostich

[57] ABSTRACT

A petroleum sulfonate is prepared by (a) separately sulfonating each of two or more different petroleum fractions boiling substantially above 700° F. by contact with sulfur trioxide under reaction conditions wherein the ratio of milliliters of sulfur trioxide to grams of aromatic components is adjusted so as to produce from each separate fraction a reaction product capable of producing upon neutralization a sulfonate having a sulfonate requirement in microemulsion below about 20 grams per 100 milliliters of microemulsion; (b) separately neutralizing the sulfonated fractions; and (c) blending the hydrocarbon sulfonates produced from two or more of the fractions in proportions sufficient to yield a product petroleum sulfonate blend useful for enhanced oil recovery.

In one embodiment four different petroleum fractions are separately sulfonated using different ratios of sulfur trioxide to aromatic content for each fraction and the sulfonated fractions are blended in a weight ratio between 0:1:1:0 and 1:10:10:1 to yield a sulfonate blend useful for enhanced oil recovery.

20 Claims, No Drawings

PROCESS FOR PRODUCING PETROLEUM SULFONATES

CROSS REFERENCE TO RELATED APPLICATIONS

This application is a continuation of application Ser. No. 912,072, filed Sept. 25, 1986, now abandoned, which is a continuation-in-part of application Ser. No. 371,992 filed on Apr. 26, 1982 now abandoned.

BACKGROUND OF THE INVENTION

The present invention relates to a process for producing petroleum sulfonates and a petroleum sulfonate blend which is useful in enhanced petroleum recovery systems.

Petroleum sulfonates are typical anionic surfactants which contain one or more sulfonate groups per molecule of sulfonated hydrocarbon. These petroleum sulfonates are useful in a variety of applications, including use as surfactants in enhanced petroleum recovery systems. Increasingly important in enhanced petroleum recovery systems is the use of petroleum sulfonates in forming micellar solutions usually comprising a brine, a hydrocarbon, petroleum sulfonate and cosurfactant.

It is known in the art to produce petroleum sulfonates by contacting a crude oil with a sulfonating agent and a neutralizing agent. Crude oils sulfonated in this manner, however, suffer from the disadvantage of containing a wide variety of aromatics and other components which are either under-sulfonated, producing a deficiency of sulfonate product, or over-sulfonated, producing an abundance of highly water soluble polysulfonates. Thus, sulfonated crude oils yield a product sulfonate which exhibits inferior properties for forming micellar solutions useful in an enhanced oil recovery system.

Sulfonation of certain petroleum stocks is known and appreciated by the prior art. But most petroleum stocks produce an undesirable fraction of low equivalent weight sulfonates that are highly water soluble. These low equivalent weight sulfonates are typically lost during enhanced oil recovery operations due to their solubility in reservoir connate waters and in the waters used during flooding operations. To alleviate the disadvantages of low equivalent weight sulfonates, U.S. Pat. No. 4,240,978 discloses a process for producing oil-soluble sulfonates from a vacuum gas oil. Water-soluble sulfonic acids are removed from the effluent of the sulfonation zone to control the percentage of low equivalent weight sulfonates. In this process a mixture of aromatic and paraffinic hydrocarbons having a molecular weight between 250 and 450 is sulfonated with sulfur trioxide. Water-soluble sulfonic acids formed during sulfonation are removed from the effluent of the sulfonation zone by decantation.

Another process for sulfonating petroleum oils, disclosed in U.S. Pat. No. 4,226,805, is designed to remove the very high equivalent weight sulfonates that tend to form a sludge insoluble in either oil or water. In this procedure sulfonates are produced by reacting sulfur trioxide with an aromatic petroleum oil admixed with a liquid sulfonic acid diluent. The resulting product mixture of sulfonated petroleum oil and sludge is allowed to stand so that the sludge settles out from the sulfonated petroleum oil.

U.S. Pat. No. 4,144,266 relates to a process for producing petroleum sulfonates by contacting whole crude oil or topped crude oil, or mixtures thereof, with sulfur trioxide. Unreacted hydrocarbon that tends to form sludge is removed from the reaction product by addition of water, and base is added to neutralize the sulfonic acids formed. Water washing the reaction product also removes the water soluble low equivalent weight sulfonates.

To provide an alternative method of controlling the equivalent weight distribution of the sulfonate product, U.S. Pat. Nos. 3,373,808 and 3,302,713 disclose a process for producing a petroleum sulfonate derived from a 500° F. to 1,500° F. boiling range fraction. Both the low boiling and the high boiling range fractions which are excluded in this process can yield sulfonates of undesirably low equivalent weight. The sulfonates are prepared by direct sulfonation of a petroleum distillate fraction boiling within the above range employing conventional techniques for the sulfonation and neutralization reactions.

U.S. Pat. No. 2,857,426 discloses a method of producing polyvalent metal petroleum oil sulfonates which comprises reacting a refined lubricating oil with a sulfonating agent in the presence of a solvent selected from sulfur dioxide or ethylene chloride. Sulfonic acids thus produced are then reacted with a polyvalent base, such as basic calcium, strontium or barium compounds.

SUMMARY OF THE INVENTION

The distribution of equivalent weights and the oil solubility of sulfonates used in enhanced oil recovery influence the cost efficiency of oil recovery operations. Production of sulfonates to be used in enhanced oil recovery requires a method whereby sulfonates having the desired oil solubility and equivalent weight distribution can be prepared from low cost petroleum feedstocks. In particular, there is need for a method of producing a petroleum sulfonate blend having the desired equivalent weight distribution and solubility properties useful in enhanced oil recovery from a single petroleum feed.

In the invention herein a process is provided for producing petroleum sulfonates from a petroleum feed by separately sulfonating each of two or more different hydrocarbon fractions boiling substantially above 700° F. by contact with sulfur trioxide under reaction conditions wherein the ratio of milliliters of sulfur trioxide to grams of aromatic components is adjusted so as to produce from each separate fraction a reaction product capable of producing upon neutralization a sulfonate having a sulfonate requirement in microemulsion below about 20 grams per 100 milliliters of microemulsion. The sulfonated fractions are separately neutralized with a neutralizing agent so as to produce from each a product sulfonate, and the hydrocarbon sulfonates produced from two or more of the fractions are blended in proportions sufficient to yield a product petroleum sulfonate blend useful for enhanced oil recovery.

DETAILED DESCRIPTION OF THE INVENTION

It is well known that the aromatic moieties in a petroleum molecule are the ones that are sulfonated. And generally, the greater the proportion of polyaromatics in a petroleum feed, the higher the proportion of polysulfonated molecules formed upon sulfonation of the feed. It has also been found that the higher the ratio of the amount of sulfonating agent to the amount of aromatic components in the feed the greater the percentage of polysulfonates formed. Since the equivalent weight of a sulfonate is defined as the molecular weight divided by the number of sulfonate groups formed per molecule, the equivalent weight of a polysulfonated molecule is generally substantially lower than the equivalent weight of a monosulfonated molecule.

Therefore the tendency of a petroleum feed to form polysulfonated molecules and hence molecules having an undesirably low equivalent weight can be controlled by controlling the conditions under which a petroleum feed or feed fraction is sulfonated. As a rule, for any given feed or feed fraction, the higher the ratio of sulfonating agent in milliliters to 100 grams of aromatic components in the feed to be sulfonated, the more polysulfonates will be formed.

Therefore, in the sulfonation step of the process of making a petroleum sulfonate, it is critical that the ratio of the amount of sulfonating agent be tailored to the amount of aromatic components in the feed or feed fraction so as to limit the formation of polysulfonates and thereby control the formation of undesirable low equivalent weight sulfonates. Using this technique the desired average equivalent weight or equivalent weight distribution for the product sulfonate formed therefrom can be achieved.

For example, where it is desirable that the equivalent weight of the sulfonate be proportionately distributed over a broad or intermediate equivalent weight range, as in the sulfonates used in enhanced oil recovery, this technique of tailoring the ratio of the sulfonating agent to the aromatic moiety of the petroleum feed can also be utilized to produce a sulfonate blend having the desired equivalent weight characteristics by fractionating and separately sulfonating the resultant fraction of a single petroleum crude. The sulfonates so produced from the feed fractions will have different average equivalent weights and are blended to achieve the desired equivalent weight distribution in the sulfonate blend.

The effect of low equivalent weight upon the ability of a sulfonate to perform is marked. It is well known in the art that low equivalent weight sulfonates, e.g., those below 300 grams per equivalent, are more water soluble than higher equivalent weight sulfonates. As a result, the low equivalent weight sulfonates in a soluble oil used in enhanced oil recovery tend to partition out of the slug of micellar solution and become lost to the reservoir or flooding waters. Medium to high equivalent weight sulfonates, on the other hand, tend to remain dissolved in the slug of micellar solution so that the micellar solution moves through the reservoir as a relatively intact slug. Dissolution of the micellar slug within the reservoir leads to inefficient oil recovery.

To achieve the best results in enhanced oil recovery operations using a micellar solution, therefore, the equivalent weight range and distribution of the sulfonate used must be carefully controlled. Sulfonation of a single petroleum feed usually does not yield a sulfonate having a satisfactory equivalent weight distribution for enhanced oil recovery. However, it has been found that such a sulfonate can be produced by fractionating a petroleum feed into two or more fractions, separately sulfonating the fractions in accordance with the invention herein, and blending all or a part of two or more of the product sulfonates so as to form a product sulfonate blend having the desired range and equivalent weight distribution.

A particularly effective blend of sulfonates for enhanced oil recovery comprises a blend of four fractions with the following equivalent weight distribution: a first fraction having an average equivalent weight in the range between 300 and 400 grams per equivalent; a second fraction having an average equivalent weight in the range between 350 and 450 grams per equivalent; a third fraction having an average equivalent weight in the range between 400 and 500 grams per equivalent, and a fourth fraction having an average equivalent weight in the range between 500 and 700 grams per equivalent.

The four fractions can be blended in any desired weight ratio between 0:1:1:0 and 1:10:10:1, but the preferred ratio of the fractions is 1:2:2:1 for the first, second, third, and fourth fractions, respectively.

To determine the optimum sulfonating conditions for any given feed or fraction of the feed, the feed is sulfonated using several different ratios of the amount of sulfonating agent to the amount of aromatic moiety therein and the quality of sulfonates is measured using two techniques: (1) test tube or vial phase behavior tests and (2) reservoir rock or sand pack core floods. In the phase behavior tests, a hydrocarbon, usually hexane; brine; sulfonate; and, optionally, a cosurfactant are mixed and equilibrated at brine salinities varying from about 0 to 10 percent by weight sodium chloride. At high salinity the surfactant is largely insoluble in the salt solution and is, therefore, in the upper hydrocarbon phase formed after equilibration in the vial. At low salinity, the surfactant is more soluble in the salt solution and is, therefore, in the lower, aqueous phase. At intermediate salinities three phases are observed, an upper hydrocarbon phase, a middle microemulsion phase containing hexane, surfactant, water, salt, and cosurfactant, if used, and a lower aqueous phase. At some intermediate salinity called the optimal salinity, the middle microemulsion phase will contain equal volumes of the hydrocarbon and brine. In vial phase behavior tests different sulfonates form microemulsions of different volumes at their optimal salinities.

It is well known in the art that in sand pack core floods one of the factors that results in good oil recovery is a sulfonate or sulfonate blend that forms the largest volume of microemulsion while requiring the smallest amount of sulfonate at its optimal salinity. The measure of the effectiveness of a sulfonate, therefore, is usually determined from vial test data by calculating the grams of sulfonate required to generate 100 milliliters of microemulsion at the optimal salinity. This measure of effectiveness is called "the height of the binodal curve" or the "sulfonate requirement." It has been found that, by separately controlling the conditions of sulfonation for each fraction of a sulfonate blend, the sulfonate requirement of a sulfonate blend can be controlled. Thus, vial tests can be used to determine the most effective sulfonating conditions for producing a blend of sulfonates for use in the soluble oils used in enhanced oil recovery from petroleum feeds.

Petroleum feedstocks suitable for use in the process herein include either natural petroleum or synthetic liquid hydrocarbons. Natural liquid petroleum suitable for use herein as feedstocks include such diverse materials as petroleum distillates and residues, gasoline, naphtha, kerosine, crude petroleum, gas oil, residual oil, tar-sand and shale oil, and mixtures thereof.

The preferred petroleum feedstocks suitable for use in the process of this invention are sulfonatable petroleum feedstocks, preferably derived from a crude oil or a topped crude oil. Crude oils are classified by the Bureau of Mines into three categories according to the predominant composition of their 736° F. to 788° F. boiling fraction as paraffinic, intermediate and naphthenic.

The term crude oil as used herein includes crude oils which have been "topped" to remove up to 40 percent of the lighter ends, with boiling points below 650° F. The preferred feedstock is a lube crude oil having an average molecular weight within the range of from 200 to 1,000.

Preferred crude oils are those having average molecular weights in the range of from about 200 to about 1,000, preferably from about 300 to about 800, and more preferably from about 350 to about 500. The percent aromatics and olefins in the crude oil composition may vary from 10 to about 95, preferably from about 20 to about 80, most preferably from about 25 to about 50 weight percent. However, since the aromatic compounds in the crude oil are the primary compounds which undergo sulfonation, it is desirable to have a high aromatic content in the crude oil, preferably above 10 weight percent.

In a preferred method of deriving the feed to the sulfonation process, a lube crude oil is first distilled or "topped" in a standard atmospheric distillation unit at a temperature of from about 650° F. to about 750° F. to produce a reduced, topped crude oil. Next, the topped lube oil is distilled in a standard high vacuum distillation unit under a vacuum of from about 1 to about 7 p.s.i.a., preferably from about 1.5 to about 3 p.s.i.a.

Vacuum gas oil is the lightest material and has a boiling point range of from about 540° F. to about 610° F. The light vacuum gas oil is not utilized as a source for petroleum sulfonates herein because the equivalent weight of the compounds derived from said vacuum gas oil is too low to be effective in certain enhanced petroleum recovery systems. Normally, the distilled vacuum gas oil is sent to a fluid catalyst cracking (FCC) unit for further processing.

Although the reduced, topped crude could be processed as a single fraction, the crude is usually distilled into two or more fractions, preferably about four, each fraction producing sulfonates having a different average molecular weight such that the resulting sulfonates can be blended to produce a sulfonate blend having a desired range and distribution of average equivalent weights useful for enhanced oil recovery.

In the preferred embodiment, the first distillate fraction is vacuum distilled from the lube oil at a temperature of from about 540° to about 890° F. with at least 50 percent by volume of the fraction boiling within the range of from about 720° F. to about 820° F. and this fraction has a typical viscosity range of from about 19 to about 30 centistokes at 100° F. This petroleum fraction is the source feed for low equivalent weight petroleum sulfonates which preferably have average equivalent weights within the range of from about 300 g/eq to about 400 g/eq.

A second distillate fraction is vacuum distilled from the lube oil at a temperature within the range of from about 670° F. to about 1,000° F. with at least 50 percent by volume of the fraction boiling within the range of from about 770° F. to about 890° F. This petroleum fraction has a viscosity of from about 30 to about 60 centistokes at 100° F. and, in addition, is the source feed for medium equivalent weight petroleum sulfonates which have equivalent weights within the range of from about 350 g/eq. to about 450 g/eq.

The third distillate fraction produced in the vacuum distillation unit is vacuum distilled from the lube oil at a temperature of from about 710° F. to about 1,090° F. with at least 50 percent by volume of the fraction boiling within the range of from about 940° F. to about 980° F., the fraction having a typical viscosity within the range of from about 80 to about 350 centistokes at 100° F. This petroleum fraction is the source feed for high equivalent weight petroleum sulfonates which have average equivalent weights within the range of from 400 g/eq. to about 500 g/eq.

The fourth distillate fraction comprises the vacuum resid from the above vacuum distillation which is sent to a standard propane deasphalting unit. This petroleum fraction comprises high boiling components including asphaltenes with at least 30 percent by volume of the fraction boiling within the range of 1,000° F. to 1,120° F.

In the deasphalting unit, the vacuum resid is contacted with liquid propane at a weight ratio of from about 1:5 to about 1:10 respectively, under conditions of a temperature of from about 100° F. to about 200° F., and a pressure of from about 200 p.s.i.g. to about 400 p.s.i.g.

The deasphalted petroleum fraction is the source feed for very high equivalent weight petroleum sulfonates which have average equivalent weights within the range of from about 500 g/eq. to about 700 g/eq. A typical viscosity for this petroleum fraction is within the range of from about 30 to about 50 centistokes at 210° F.

Vial tests are typically conducted to determine which set of sulfonation conditions produces a sulfonate having the desired sulfonate requirement and/or optimal salinity. Generally, when fractionated and sulfonated in accordance with the teachings herein, petroleum feeds containing the requisite amount of aromatic compounds will produce sulfonates having a sulfonate requirement at least 50% less than the sulfonate requirement of a sulfonate produced by a similar method of sulfonation from the same petroleum feed but without fractionation of the feed and separate sulfonation of the feed fractions in accordance with the teachings herein regarding the appropriate ratios of sulfonating agent to feed aromatic content for each of the feed fractions.

Although the exact mechanism involved that results in lowered sulfonate requirement when the feed is fractionated and the fractions of the feed are separately sulfonated is unknown, it is believed that during separate sulfonation of the fractions monoaromatic moieties in the hydrocarbon molecule are more readily sulfonated so that a higher percentage of the monoaromatics in each fraction are sulfonated, resulting in a higher yield of monosulfonates for the total feed than would result if the feed were sulfonated using the same sulfonation procedure but without fractionation.

After the fractionation step, sulfonation of one or more different hydrocarbon fractions is performed using standard equipment and techniques.

The term sulfonation as used herein designates any procedure by which a sulfonic acid group ($-SO_2OH$) or corresponding salt or sulfonyl halide is attached to a carbon atom. Sulfonates are classified according to the group to which the $-SO_3$ is attached. Sulfonating agents which are suitable for use herein include sulfur trioxide and fuming sulfuric acid, the latter of which comprises sulfur trioxide dissolved in sulfuric acid, but sulfur trioxide is the preferred sulfonating agent. Sulfonation is generally carried out directly by separately contacting the petroleum fractions with a sulfonating agent under reaction conditions. Since the sulfonation reaction herein is extremely rapid, it is desirable to first dilute the petroleum fraction with sulfur dioxide or a $C_1$ to $C_6$ halogenated hydrocarbon which acts as a viscosity control agent and thermal diluent for the reaction, and, in addition, reduces side reactions in the sulfonation process. Preferred $C_1$ to $C_6$ halogenated hydrocarbons are selected from methylene chloride, ethylene chloride, ethyl chloride, n-propyl chloride, isopropyl chloride, n-butyl chloride, isobutyl chloride, hexyl fluoride or a mixture thereof. Preferably, the petroleum fraction and $C_1$ to $C_6$ halogenated hydrocarbon are admixed in a weight ratio range of from about 1:0 to about 1:10, especially from about 1:0.1 to about 1:3.

The diluted petroleum fraction is contacted with the sulfonating agent at a concentration sufficient to monosulfonate the aromatic compounds in the petroleum fraction. In general, the amount of sulfonating agent used will depend upon the aromatic content of the petroleum fraction, since the aromatic compounds are the primary compounds undergoing sulfonation in the reaction. Thus, the sulfur to aromatic compound ratio is important in determining the degree of sulfonation in the reaction. In general, the amount of sulfonating agent used in the reaction comprises from about 0.02 to about 1.5 grams of sulfonating agent per gram of petroleum fraction(s) used in the reaction.

Generally, the sulfonating step comprises separately sulfonating one or more different petroleum fractions by contact with a sulfonating agent so as to produce a substantial proportion of monosulfonates in each hydrocarbon oil fraction. Preferably no less than 40 percent of the sulfonates so formed are monosulfonates. The sulfonation step can be conducted using either batch or continuous feed reactions. However, generally in batch sulfonation reactions some of the sulfonating agent fed into the reactor is lost to the reaction so that the amount of sulfonating agent fed into the reactor is larger than the amount required to sulfonate the aromatic moiety of the petroleum fraction.

It should also be noted that each petroleum fraction contains a different distribution of aromatic compounds; thus the amount and rate of contact of sulfonating agent used in the reaction will vary in accordance with the aromatic content of the petroelum fraction undergoing sulfonation.

In general, the ratio of sulfonating agent to the aromatic components of the feed fraction should be sufficient to produce a sulfonate from that fraction having in microemulsion a sulfonate requirement below about 20 grams per 100 milliliters of microemulsion. In the preferred embodiment wherein the feed is fractionated into the above described first, second, third and fourth fractions, the sulfonating agent is sulfur trioxide and the ratio of sulfur trioxide to the aromatic content in each fraction is controlled as follows: in the first fraction, the ratio is between 5.0 and 8.0 milliliters of sulfur trioxide per 100 grams of aromatic moiety; in the second fraction, the ratio is between 2.0 and 4.0 milliliters of sulfur trioxide per 100 grams of aromatic moiety; in the third fraction the ratio is between about 3.0 and 5.0 milliliters of sulfur trioxide per 100 grams of aromatic moiety; and in the fourth fraction the ratio is between about 4.0 and 7.0 milliliters of sulfur trioxide per 100 grams of aromatic moiety in the feed.

When sulfur trioxide is used as the sulfonating agent, as in the preferred embodiment, the sulfur trioxide is heated to a temperature of from about 0° F. to about 400° F., preferably from about 100° F. to about 180° F. to facilitate formation of gaseous sulfur trioxide. Next, an inert carrier gas, for example nitrogen or air, is utilized to sweep the gaseous sulfur trioxide into contact with the petroleum fraction.

Reaction conditions include temperatures within the range of from about 80° F. to about 400° F.; however, reaction temperatures greater than 250° F. may result in undesirable charred products. The preferred reaction pressure is atmospheric pressure, but pressures up to 150 p.s.i.g. may be used without deleterious effect upon the sulfonation reaction.

In the usual case sulfonation further comprises separately neutralizing the one or more different petroleum or fractions to form a sulfonated product.

Neutralizing agents used usually comprise an aqueous basic solution containing a monovalent or divalent cation. Suitable neutralizing agents include aqueous solutions of sodium hydroxide, ammonium hydroxide, barium hydroxide or calcium hydroxide, lithium hydroxide, potassium hydroxide, sodium carbonate, lithium carbonate, magnesium hydroxide, ammonium carbonate or magnesium carbonate, or mixtures thereof. The preferred neutralizing agents are sodium hydroxide or ammonium hydroxide. The pH of the reaction mixture during the neutralization reaction is maintained at about 3 to about 14, preferably from about 10 to about 13 and at a temperature below 175° F., preferably from about 20° F. to about 175° F. After neutralization of the petroleum sulfonic acids, a petroleum sulfonate is produced which is optionally recovered by extraction from the sulfonated product with a solvent, preferably with a mixture of a $C_3$ to $C_{10}$ aliphatic hydrocarbon and an aqueous solution of a $C_1$ to $C_5$ alcohol or a polar solvent, the extraction usually being performed with a weight ratio of petroleum sulfonate to $C_3$ to $C_{10}$ aliphatic hydrocarbon to $C_1$ to $C_5$ alcohol or polar solvent between about 1:0:0.1 and about 1:30:1,000, preferably between 1:0:0.5 to about 1:10:100. Desirable $C_3$ to $C_{10}$ aliphatic hydrocarbons include pentane, hexane, heptane, octane, nonane or decane or a mixture thereof. Pentane is the preferred aliphatic hydrocarbon.

The $C_1$ to $C_5$ alcohol or polar solvent is usually selected from methanol, ethanol, propanol, isopropanol, benzene, or toluene, or a mixture thereof. The preferred alcohol is isopropanol.

Alternatively, the petroleum sulfonated product is not extracted, but is subjected to water washing using known techniques to remove undesirable low equivalent weight sulfonates that will readily dissolve in the water and be washed away.

In the preferred embodiment the various petroleum fractions are separately sulfonated, neutralized and extracted (or water washed) to produce sulfonates having a range of equivalent weights between 300 and 700 grams per equivalent. The petroleum sulfonates produced herein can be blended together and/or blended with other suitable sulfonates to provide a surfactant slug having a distribution of equivalent weights within the above range that is useful in an enhanced petroleum recovery process as described herein. But preferably, four petroleum fractions are admixed at a ratio range of from about 0:1:1:0 to about 1:10:10:1. In some sulfonate preparations, especially those having a sulfonate activity of at least about 40 grams of sulfonate in every 100 grams of sulfonated product remaining after the neutralization step, it is desirable to prepare the petroleum sulfonates without utilizing an extraction step in the process. Thus, the petroleum fraction may be sulfonated, neutralized, water-washed, and blended into the desired composition to achieve a product sulfonate or sulfonate blend having a desirable equivalent weight range and distribution for enhanced oil recovery.

If the feeds or feed fractions used in this invention have an aromatic content of between 55 and 80 weight percent, the sulfonated product yielded by separately sulfonating the feeds in many instances (depending upon the conditions of sulfonation selected) has an activity (grams of sulfonate in 100 grams of sulfonated product) as high as many commercial sulfonate preparations when the sulfonated and neutralized product is merely water-washed to remove the low equivalent weight components rather than being extracted with solvent. Therefore in one embodiment of this invention, in the preparation of sulfonates yielded by this invention, water-washing can be substituted for solvent extraction with a savings in total cost of preparing the sulfonates of as much as 30 percent depending on the price of energy. Preferably, water-washing is substituted for solvent extraction when the activity of the sulfonate product is at least 40 percent.

In general, the petroleum sulfonates disclosed herein are suitable for use in enhanced petroleum recovery systems. The typical enhanced petroleum recovery system is based upon the use of a surfactant slug of soluble oil which contains a broad range of equivalent weight sulfonates. The equivalent weight range of the sulfonate blend is usually from about 300 g/eq. to about 700 g/eq., but the optimal distribution or character will vary according to the characteristics and properties of the oil reservoir selected to undergo an enhanced petroleum recovery process. It is known, for example that high equivalent weight sulfonates are required for low interfacial tension and that low equivalent weight sulfonates are required for water and oil-water solubility in an enhanced petroleum recovery process. Sulfonates having equivalent weights lower than 300 are generally undesirable because of their extreme water solubility. They tend to move ahead of the soluble oil slug front with the flowing water phase. Petroleum sulfonates having too high equivalent weights, i.e., above 700 g/eq., are generally too oil soluble and tend to be retained in the rock behind the oil slug.

In particular, the precise blend of petroleum sulfonates to be used in a micellar solution in an enhanced petroleum recovery process is discovered empirically by first determining the optimal salinity of the sulfonate blend in a brine containing monovalent ions or salts, usually sodium chloride, sodium carbonate, etc. Generally, the brine solution used to determine optimal salinity of the sulfonate blend approximates in composition the brine found in the reservoir to undergo an enhanced oil recovery process. The optimal salinity for the sulfonate or sulfonate blend is discovered by mixing determined concentrations of a hydrocarbon, petroleum sulfonate, cosurfactant and brine, said brine usually containing a determined concentration of salt, until the hydrocarbon phase and aqueous phase are in equilibrium as is described in greater detail above. At optimal salinity, the microemulsion phase contains equal amounts of oil and brine. Once the optimal salinity of the sulfonated blend has been found, the sulfonate requirement at optimal salinity can be calculated. In addition, core samples from strategic locations within the reservoir are taken to determine pore volume, reservoir composition, and the kind of cations located in the reservoir, etc.

After all of the data generated from the collected samples are analyzed, a core flooding test is performed to determine the effectiveness of a petroleum sulfonate for recovering oil from a representative core. The best sulfonate or sulfonate blend is the one that achieves highest oil recovery with lowest sulfonate requirement.

Thus, a second measure of the effectiveness of petroleum extract sulfonates is the height of the binodal curve, or the sulfonate requirement. As used herein the terms "height of the binodal curve" and "sulfonate requirement" indicate the grams of sulfonate required to produce 100 milliliters of microemulsion containing an aqueous component at the optimal salinity of the sulfonate as determined above by vial test. The "sulfonate requirement" number indicates the effectiveness of the sulfonate for producing microemulsions. Thus a sulfonate having a lower "sulfonate requirement" number is superior for enhanced oil recovery to one having a higher sulfonate requirement number. When the sulfonate is to be used in a reservoir having a relatively high salinity of the connate waters, the sulfonating conditions may be selected primarily to achieve a suitable optimal salinity with the sulfonate requirement being of secondary consideration. The conditions of sulfonating, therefore, should be selected to yield the desired sulfonate requirement and/or optimal salinity in the sulfonate as determined by vial tests and the conditions in the reservoir to be treated. Most preferably the sulfonated fractions blended to form a sulfonate blend each have a sulfonate requirement in microemulsion below about 12 grams per 100 milliliters of microemulsion at optimal salinity below about 7 and the sulfonate blend so formed has a sulfonate requirement below about 8 at optimal salinity below about 4.

The invention is further illustrated by the following examples which are illustrative of various aspects of the invention and are not intended as limiting the scope of the invention as defined by the appended claims.

EXAMPLES 1 to 13

To demonstrate the effect upon sulfonate requirement and optimal salinity of the ratios of sulfonating agent to feed and to aromatic content in the feed, a series of experiments were conducted using various sulfonating ratios in a batch sulfonation reaction. Four petroleum fractions were prepared from a blend of 50.2 weight percent Intermediate Sweet West Texas (ISWT) lube crude oil and 49.8 weight percent of Van lube crude oil obtained from the Van oil field in Texas. Table 1 shows the boiling point distributions of the components of the four fractions.

Four petroleum fractions of Table 2, the 100, 170, 600 and deasphalted oil fractions from the vacuum distillation column and deasphalting column, were separately sulfonated and neutralized using the ratios of sulfur trioxide to the aromatic content of the feed summarized in Table 2 in accordance with the following procedure.

The petroleum fraction was dissolved in 1,2-dichloroethane and placed in a 2 liter three-necked flask equipped with a mechanical stirrer, a gas inlet tube, and a reflux condenser. Sulfur trioxide was placed into a 500 milliliter three-necked flask connected to the 2 liter flask with a Tygon tube. The flask containing the sulfur trioxide was heated to 55° C. while nitrogen gas was passed through it at a rate of 8 standard cubic feet per hour to sweep the sulfur trioxide into the reaction flask.

A water bath was used to keep the reaction temperature below 50° C.

The product formed by reaction of the feed and the sulfur trioxide was neutralized with 10 molar sodium hydroxide to a final pH of 11.4. About 400 milliliters of pentane and 400 ml of 40 percent isopropyl alcohol were added.

The lower layer of isopropyl alcohol/water was separated off using a separatory funnel. The upper layer was then extracted two more times with 600 ml of 40 percent isopropyl alcohol. The layers of isopropyl alcohol were combined and dried in an oven at 80° C. The resulting solid was extracted with two liters of a hot, 85 percent concentration of isopropyl alcohol and the extract was filtered through filter paper using a Buchner funnel.

The filtrate was dried in an oven at 80° C. overnight. The properties of the sulfonates yielded are summarized in Table 2.

TABLE 1

| Volume % | First Petroleum Fraction, °F. | Second Petroleum Fraction, °F. | Third Petroleum Fraction °F. | Vacuum Resid Temp. Profile °F. |
|---|---|---|---|---|
| IBP | 547 | 674 | 614 | 718 |
| 5 | 702 | 746 | 830 | 961 |
| 10 | 712 | 763 | 868 | 1010 |
| 20 | 724 | 786 | 914 | 1038 |
| 30 | 733 | 802 | 936 | 1046 |
| 40 | 746 | 824 | 949 | 1054 |
| 50 | 757 | 844 | 963 | 1089 |
| 60 | 770 | 864 | 976 | 1117 |
| 70 | 808 | 880 | 989 | |
| 80 | 838 | 902 | 1011 | |
| 90 | 860 | 933 | 1040 | |
| EP/ | 892/ | 981/ | 1082/ | 1122/ |
| % REC | 99.0 | 99.0 | 98.0 | 67.0 |

IBP = Initial Boiling Point
EP = End Point
% REC = percent recovered content varied from zero to 10 weight percent sodium chloride. To make the sulfonate solutions, 3 grams of the sulfonate, and 1.5 milliliters of Butyl Cellusolve ™ sold by Union Carbide were dissolved in distilled water to give a total volume of 100 milliliters at 110° F. A 5 milliliter aliquot of the sulfonate solution was mixed with 2.5 milliliters of brine and 5 milliliters of hexane in a 15 milliliter graduated cylinder and the cylinder was sealed with a cap. Cylinders containing the samples of sulfonate solution were placed in a water bath and allowed to equilibrate for several days at 110° F. Upon equilibration, the mixtures in the graduated cylinders had separated into two or three layers. At low salinity, an oil layer and a microemulsion layer formed. At high salinity, an aqueous layer and a microemulsion formed. And at intermediate brine salinity, a microemulsion layer, an oil layer, and an aqueous layer formed.

To determine the optimal salinity, measurements were made of the amounts of water and of oil contained in each microemulsion. The optimal salinity is determined by finding the microemulsion that contains equal volumes of water and oil. The sulfonate requirement of the sulfonate sample is then determined by calculating the grams of sulfonate that would be contained in 100 milliliters of the microemulsion at optimal salinity. Results of the calculations to determine the optimal salinity and the sulfonate requirement of the sulfonate samples are summarized in Table 2.

As can be seen from the data in Table 2, the best sulfonate for enhanced oil recovery is selected by determining for each feed fraction which sulfur trioxide to aromatic content ratio yields the sulfonate having the highest equivalent weight at the optimal salinity nearest that of the reservoir desired to be treated and/or having the lowest sulfonate requirement. For example, for the second fraction (Example 4) the ratio of 1.71 ml of sulfur trioxide to 100 grams of aromatic content in the feed yields a sulfonate having an equivalent weight of 415, an optimal salinity of 2.9 and a sulfonate require-

TABLE 2

| Feed Source | Ex. No. | SO$_3$ to Feed (ml/100 gm) | SO$_3$ to Feed Aromatics (ml/100 gm) | Mono/Poly[3] Ratio | % Aromatic Content | Equivalent[1] Weight, g/eq. | Sulfonate Requirement (gm/100 ml) | Optimal Salinity |
|---|---|---|---|---|---|---|---|---|
| First Petroleum Fraction | 1 | 1.71 | 5.48 | 82.5/17.5 | 31.2 | 367 | 20.4 | 8.6 |
| | 2 | 3.43 | 10.99 | 46.1/53.9 | 31.2 | 368 | 20.0 | 10.0 |
| | 3 | 6.83 | 21.87 | 77.4/22.6 | 31.2 | 398 | 28.0 | 8.0 |
| Second Petroleum Fraction | 4 | 1.71 | 4.58 | 72.9/27.1 | 34.3 | 415 | 7.03 | 2.9 |
| | 5 | 3.43 | 9.20 | 70.8/29.2 | 34.3 | 416 | 9.38 | 4.0 |
| | 6 | 6.83 | 18.31 | 53.1/46.9 | 34.3 | 398 | 13.44 | 6.0 |
| Third Petroleum Fraction | 7 | 0.85 | 2.15 | — | 39.5 | 273 | 22.6 | 10.0 |
| | 8 | 1.71 | 4.31 | 58.2/41.8 | 39.7 | 498 | 7.7 | 0.33 |
| | 9 | 3.43 | 8.64 | 55.4/44.6 | 39.7 | 479 | 5.3 | 0.45 |
| | 10 | 6.80 | 17.23 | — | 39.5 | 503 | < | (?) |
| Fourth[2] Petroleum Fraction (Vacuum Resid) | 11 | 2.50 | — | 38.3/61.8 | — | 558 | < | <0 |
| | 12 | 5.00 | — | 22.4/77.6 | — | 531 | < | <0 |
| | 13 | 7.50 | — | 17.2/82.8 | — | 498 | < | <0 |

[1] Determined by the Stepan 299 tests in which the isolated sulfonate is ashed with sulfuric acid and the resulting sodium sulfonate is weighed.
[2] The vacuum resid fraction is deasphalted by contact with propane before the sulfation reaction.
< Too oil soluble to form a micellar solution.
[3] The mono and polysulfonates are separated by gradient elution ion exchange high performance liquid chromatography recorded using a VV detector at 254 nm. The relative peak areas of mono and polysulfonates are measured.

The equivalent weight, optimal salinity and sulfonate requirement of the sulfonates prepared from the above-described petroleum fractions (Table 1) by sulfonating under various conditions are summarized in Table 2. The optimal salinity and sulfonate requirements of the sulfonated fractions were determined as follows. To evaluate the phase behavior of each of the sulfonates, in vial tests a series of eleven sulfonate solutions was prepared for each sulfonate, each solution having a brine ment of 7.03 grams of sulfonate per 100 milliliters of microemulsion. For a reservoir having a low saline connate water, this sulfonate would be preferred for enhanced oil recovery. However, in a high saline reservoir, the sulfonate of example 5 may be preferred for its optimal salinity of 4.0, even though the equivalent weight of 416 is lower and the sulfonate requirement of 9.38 is higher.

Comparison of the properties of examples 1 to 13 also shows that the sulfonates formed from the first and fourth fractions possess less desirable solubility properties for the formation of microemulsions than do the second and third fractions. Examples 1 to 4 are too water soluble and examples 11 to 13 are too oil soluble.

EXAMPLE 14

A blend of petroleum sulfonates produced in accordance with the procedure of Examples 1 to 13 is prepared by admixing the sulfonates of Example 2, having an average equivalent weight of 368, Example 5, having an average equivalent weight of 416, Example 9, having an average equivalent weight of 479, and Example 12, having an average equivalent weight of 531, in a weight ratio of 1:2:2:1, respectively. The overall average equivalent weight of the sulfonate blend is 460. The optimal salinity and height of the binodal curve of the sulfonate blend is determined an compared with two commercially available petroleum sulfonates by dissolving 9 grams of the sulfonate described in Table 3 below, 1 gram of ethylene glycol menobutyl ether and the designated weight of sodium chloride (Table 3) in distilled water to a total volume of 100 ml. Next 7.5 ml of the sulfonate solution is mixed with 5 ml of hexane in a 15 ml Pyrex vial and equilibrated in a 110° F. water bath for 2 days.

The volumes of the oil, brine and microemulsion phases in the Pyrex vial are recorded after the phases have separated and the phase boundaries have cleared and the optical salinity of the sulfonates and sulfonate requirements are calculated.

TABLE 3

| Sulfonate Blend | Optimal Salinity (Wt. % NaCl) | Sulfonate Requirement (gm/100 ml) |
| --- | --- | --- |
| Example 14 | 1.8 | 5.43 |
| Stepan[1] | 1.6 | 11.75 |
| Exxon[2] | 1.6 | 6.43 |

[1]Blend of petroleum sulfonates having an average equivalent weight of 450 and produced commercially by The Stepan Corporation.
[2]Blend of petroleum sulfonates having an average equivalent weight of 375 and produced commercially by The Exxon Corporation.

As can be seen from the data in Table 3, while the optimal salinity of the sulfonate blend of Example 20 herein has a an average molecular weight equal to or higher than and an optimal salinity only slightly higher than either the Exxon or Stepan sulfonates, the sulfonate requirement of the sulfonate of Example 14 is 1 gram per 100 milliliters of micellar solution lower than those of the commercial sulfonates. Since the sulfonate is the most expensive ingredient in a micellar solution, a savings of 1 gram per 100 milliliters of microemulsion is a substantial savings in an oil recovery operation.

EXAMPLE 15

An unfractionated Louisiana Sweet crude oil was sulfonated by charging 1,000 ml of the crude oil into a 2 liter, three-necked, round-bottomed flask, equipped with a water cooled condenser and mechanical stirrer. The crude oil was pretreated by adding one volume of 20 percent oleum per thirty volumes of crude oil.

The sludge produced by the pretreatment was discarded and the remaining 713.9 grams of pretreated, crude oil was sulfonated by adding 65 percent oleum to the pretreated crude oil. The petroleum sulfonate thus produced was neutralized with 600 ml of ammonium hydroxide and transferred to a separatory funnel. The bottom petroleum sulfonate layer was collected and dried.

The equivalent weight of the product sulfonate was indeterminate because it was insoluble in chloroform and thus could not be passed through the liquid-solid chromatographic column used to separate the petroleum sulfonate from other components.

EXAMPLES 16-35

Four different fractions of a light Louisiana sweet crude oil boiling within the range of 800° to 1000° F. were analyzed according to the procedure of ASTM: Designation 1160-77 by testing one quart samples of each petroleum fraction.

The results are summarized in Table 4.

The four petroleum fractions described in Table 4 were separately sulfonated and neutralized using the ratios of sulfur trioxide to feed and of sulfur trioxide to aromatic content disclosed in Table 5 and in accordance with the following procedure. Each petroleum fraction was dissolved in 1,2-dichloroethane and placed in a 2 liter, three-necked, round-bottomed flask, equipped with a water cooled condenser and mechanical stirrer. Next, sulfur trioxide was placed in a 500 ml three necked flask connected to the 2 liter flask with a Tygon tube. The sulfur trioxide was heated to 140° F. and nitrogen gas was passed over it at a rate of 8 standard cubic feet (SCF)/hr to sweep the sulfur trioxide into the 2-liter reaction flask. An ice bath was used to keep the reaction temperature below 122° F.

The sulfonic acid product of each petroleum fraction was separately neutralized by adding 400 ml of 10M sodium hydroxide in a 50 percent isopropanol/water solution to the sulfonic acid product. The final pH was 11.4. The neutralized solution was transferred to a separatory funnel and the solution was allowed to separate. The product sulfonate was recovered and dried using the procedure described for Examples 1 to 13 above. Properties of the four sulfonated fractions are summarized in Table 5.

A sulfonate blend having properties desirable for use in enhanced oil recovery was formulated by combining the sulfonates of Examples 18, 22, 27 and 35 in a weight ratio of 1:2:2:1, respectively. The average equivalent weight of the sulfonate blend was 454 grams/eq, the optimal salinity was 1.4 and the sulfonate requirement was 9.14 grams per 100 milliliters of microemulsion.

EXAMPLE 17

A petroleum sulfonate was prepared using a distillate of light Louisiana sweet crude oil boiling within the range of 800° to 1000° F. A charge of 830 ml of the crude oil was placed into a 2 liter, three-necked, round-bottomed flask, equipped with a water cooled condenser and mechanical stirrer. Then 105 ml of 20 percent oleum was added to the 2 liter flask. The sulfonic acid product was neutralized by adding 400 ml of 10 M sodium hydroxide in a 50 percent isopropanol/water solution to the sulfonic acid product. The final pH was 8.9.

The neutralized solution was transferred to a separatory funnel and the solution was allowed to separate into three layers, namely, a top petroleum sulfonate layer, a middle thin waxy layer and a bottom sludge-aqueous layer. The top petroleum sulfonate layer was separated from the two lower layers and the two lower layers were discarded.

To extract the product, 228 ml of a 50 percent isopropanol/water solution was added to the petroleum sulfonate layer in the separatory funnel. The mixture was shaken vigorously and allowed to settle into a top oil layer and a bottom aqueous-isopropanol, petroleum sulfonate layer. The bottom aqueous-isopropanol, petroleum sulfonate layer was collected and dried. The yield of petroleum sulfonate was 203 grams. The equivalent weight of the product petroleum sulfonate was 265 grams/eq.

TABLE 4

| Feed Source | Oil (g) | SO$_3$ (ml) | Ethylene Dichloride (ml) | Yield (g) | Equivalent (1) Weight, g/eq |
|---|---|---|---|---|---|
| First Petroleum Fraction | 400 | 27.0 | 300 | 167.0 | 370 |
| Second Petroleum Fraction | 800 | 13.5 | 300 | 112.9 | 417 |
| Third Petroleum Fraction | 400 | 13.7 | 300 | 103.2 | 471 |
| Fourth Petroleum Fraction (2) (Vacuum Resid) | 400 | 10 | 399 | 66.6 | 555 |

(1) Determined by the Stephan 299 test in which the isolated sulfonate is ashed with sulfuric acid and the resulting sodium sulfonate is weighed.
(2) The vacuum resid fraction is deasphalted by contact with propane prior to sulfonation.

TABLE 5

| Feed Source | Ex. No. | SO$_3$ to Feed (ml/100 gm) | SO$_3$ to Feed Aromatics (ml/100 gm) | Mono/Poly Ratio(3) | % Aromatic Content | Equivalent(1) Weight g/eq. | Sulfonate Requirement (gm/100 ml) | Optimal Salinity |
|---|---|---|---|---|---|---|---|---|
| First Petroleum Fraction | 16 | 3.38 | 1.16 | 68.2/31.8 | 29.1 | 374 | > | >10.0 |
|  | 17 | 6.75 | 11.6 | — | 29.1 | — | — | — |
|  | 18 | 6.75 | 23.2 | 49/51 | 29.1 | 370 | 18.0 | 9.0 |
|  | 19 | 10.25 | 35.2 | 24/76 | 29.1 | 300 | > | >10.0 |
| Second Petroleum Fraction | 20 | 0.84 | 2.6 | 82.4/17.6 | 32.3 | 425 | 8.32 | 1.8 |
|  | 21 | 0.84 | 2.6 | 65.8/35.2 | 32.3 | 425 | 4.17 | 1.3 |
|  | 22 | 0.84 | 2.9 | 66/34 | 32.3 | 465 | 5.5 | 1.4 |
|  | 23 | 1.70 | 5.9 | 58/42 | 32.3 | 417 | 10.5 | 3.8 |
|  | 24 | 3.38 | 11.8 | 55/45 | 32.3 | 418 | 11.8 | 6.2 |
|  | 25 | 6.83 | 21.1 | 53.7/46.3 | 32.3 | 382 | 13.4 | 8.0 |
| Third Petroleum Fraction | 26 | 3.43 | 8.8 | 57.8/42.2 | 38.9 | 453 | — | — |
|  | 27 | 3.42 | 12.0 | 54/46 | 38.9 | 471 | 5.1 | 0.7 |
|  | 28 | 6.84 | 24.0 | 42/58 | 38.9 | 432 | 7.6 | 1.3 |
|  | 29 | 10.25 | 36.0 | 19/81 | 38.9 | 387 | 29.3 | 6.4 |
|  | 30 | 10.3 | 26.5 | 30.7/69.3 | 38.9 | 392 | — | — |
|  | 31 | 10.3 | 26.5 | 21.7/78.3 | 38.9 | 392 | — | — |
| Fourth(2) Petroleum Fraction | 32 | 2.50 | 4.6 | 39.4/60.6 | 54.5 | 523 | — | — |
|  | 33 | 2.50 | 4.6 | 42/58 | 54.5 | 555 | < | <0 |
|  | 34 | 5.00 | 9.2 | 33/67 | 54.5 | 485 | < | <0 |
|  | 35 | 7.50 | 13.8 | 19/81 | 54.5 | 448 | < | <0 |

(1)Determined by the Stepan 299 tests in which the isolated sulfonate is ashed with sulfuric acid and the resulting sodium sulfonate is weighed.
(2)The vacuum resid fraction is deasphalted by contact with propane before the sulfonation reaction.
(3)Mono- and polysulfonates are separated by gradient elution ion exchange high performance liquid chromatography using a UV detector at 254 nm. The relative peak areas of the mono- and polysulfonates are measured.
> Too water-soluble.
< Too oil-soluble.

We claim:

1. A process for producing a petroleum sulfonate comprising:
   (a) separately sulfonating each of two or more different petroleum fractions from a single source boiling substantially above 700° F., the petroleum fractions having different aromatic contents and at least one of said petroleum fractions being obtained from a deasphalting unit, by contact with sulfur trioxide under reaction conditions wherein the ratio of milliliters of sulfur trioxide to grams of aromatic components is adjusted so as to produce from each separate fraction a reaction product capable of producing upon neutralization a sulfonate having a sulfonate requirement in microemulsion below about 20 grams per 100 milliliters of microemulsion;
   (b) separately reacting the sulfonated fractions obtained from step (a) with a neutralizing agent so as to produce from each a product sulfonate;
   (c) blending the petroleum sulfonates produced from two or more of said fractions in proportions sufficient to yield a product petroleum sulfonate blend useful for enhanced oil recovery.

2. A process for producing a petroleum sulfonate comprising:
   (a) separately sulfonating each of two or more different petroleum fractions from a single source boiling substantially above 700° F., the petroleum fractions having different aromatic contents and at least one of the petroleum fractions being obtained from a deasphalting unit, by contact with sulfur trioxide under reaction conditions wherein the ratio of milliliters of sulfur trioxide to grams of aromatic components is adjusted so as to produce from each separate fraction a reaction product capable of producing upon neutralization a sulfonate having a sulfonate requirement in microemulsion below about 12 grams per 100 milliliters of microemulsion at optimal salinity below about 7;
   (b) separately reacting the sulfonated fractions obtained from step (a) with a neutralizing agent to produce product sulfonates;
   (c) blending the petroleum sulfonates produced from two or more of said fractions in proportions sufficient to yield a product petroleum sulfonate blend having a sulfonate requirement below about 8 at optimal salinity below about 4.

3. The process defined in claim 2 wherein the neutralizing agent is a member selected from the group consisting of sodium hydroxide, ammonium hydroxide, lithium hydroxide, potassium hydroxide, sodium carbonate, ammonium carbonate and lithium carbonate and mixtures thereof.

4. The process defined in claim 2 wherein the petroleum sulfonates blended in step (c) include those derived from a fraction in step (a) comprised of components at least 90 percent by volume of which boil above 700° F. and 50 percent by volume boil within the range of 720° F. to 820° F.

5. The process defined in claim 2 wherein the petroleum sulfonates blended in step (c) include those derived from a fraction produced in step (a) comprised of components, at least 90 percent by volume of which boil above 700° F. and 50 percent by volume boil within the range of 770° F. to 890° F.

6. The process defined in claim 2 wherein the petroleum sulfonates blended in step (c) include those derived from a fraction produced in step (a) comprised of components, at least 90 percent by volume of which boil above about 700° F. and 50 percent by volume boil in the range of 880° F. to 1,000° F.

7. The process defined in claim 2 wherein the petroleum sulfonates blended in step (c) include those derived from a fraction produced in step (a) comprised of components, at least 90 percent by volume of which boil above 700° F. and 30 percent by volume boil in the range of 1,000° F. to 1,120° F.

8. The process defined in claim 2 wherein the petroleum fractions of step (a) contain from about 10 to about 80 percent aromatics.

9. The process defined in claim 2 wherein the product petroleum sulfonate has an average equivalent weight within the range of from about 300 g/eq. to about 700 g/eq. with at least 50 percent of the sulfonates having equivalent weight within the range of from about 300 g/eq. to about 450 g/eq.

10. A process for producing a petroleum sulfonate comprising:
(a) separately sulfonating four or more different petroleum oil fractions boiling substantially above 700° F., the petroleum fractions having different aromatic contents and at least one of the petroleum oil fractions being obtained from a deasphalting unit, by contact with sulfur trioxide under reaction conditions wherein the ratio of milliliters of sulfur trioxide under reaction conditions wherein the ratio of milliliters of sulfur trioxide to grams of aromatic components is adjusted so as to produce from each separate fraction a reaction product capable of producing upon neutralization a sulfonate having a sulfonate requirement in microemulsion below about 20 grams per 100 milliliters of microemulsion, at least one of the petroleum oil fractions having an average molecular weight below 500;
(b) blending the sulfonated hydrocarbon oil fraction having an average molecular weight below 500 with one or more different sulfonated hydrocarbon oil fractions; and
(c) neutralizing the blended sulfonated fractions obtained from step (b) by reaction with a neutralizing agent so as to produce petroleum sulfonates in each of the fractions blended, said sulfonating in step (a) and neutralizing being such that a product petroleum sulfonate blend is produced having at least 40 percent of the sulfonates being monosulfonates.

11. A process for producing a petroleum sulfonate comprising:

(a) separately sulfonating at least four different petroleum oil fractions boiling substantially above 700° F. selected from the group consisting of:
(1) a first fraction comprised of components at least 90 percent by volume of which boil above 700° F. and 50 percent by volume boil within the range of 720° F. to 820° F., said first fraction being sulfonated by contact with sulfur trioxide in a ratio of between about 5.0 and 8.0 milliliters of sulfur trioxide to 100 grams of aromatic compounds contained within said first fraction;
(2) a second fraction comprised of components at least 90 percent by volume of which boil above 700° F. and 50 percent by volume boil within the range of 770° to 890° F., said second fraction being sulfonated by contact with sulfur trioxide in a ratio of between about 2.0 and 4.0 milliliters of sulfur trioxide to 100 grams of aromatic compounds contained within said second fraction;
(3) a third fraction comprised of components at least 90 percent by volume of which boil above about 700° F. and 50 percent by volume boil in the range of 880° F. to 1000° F., said third fraction being sulfonated by contact with sulfur trioxide in a ratio of between about 3.0 and 5.0 milliliters of sulfur trioxide to 100 grams of aromatic compounds contained within said third fraction;
(4) a fourth fraction obtained from a deasphalting unit comprised of components at least 90 percent by volume of which boil above about 700° F. and 30 percent by volume boil in the range of 1000° to 1120° F., said fourth fraction being sulfonated by contact with sulfur trioxide in a ratio of between about 4.0 and 7.0 milliliters of sulfur trioxide to 100 grams of aromatic compounds contained within said fourth fraction;
(b) neutralizing the sulfonated fractions obtained from step (a) by reaction with a neutralizing agent so as to produce petroleum sulfonates in each of the fractions;
(c) blending the sulfonated fractions obtained from step (b) in a ratio between 0:1:1:0 and 1:10:10:1 for the first, second, third, and fourth fractions, respectively, to produce a product sulfonate blend.

12. The process of claim 1 wherein the product sulfonate blend has an average equivalent weight within the range of from about 300 g/eq. to about 700 g/eq. with at least 50 percent of the sulfonates having equivalent weight within the range of from about 300 g/eq. to about 450 g/eq.

13. The process defined in claim 12 wherein the neutralizing agent is a member selected from the group consisting of sodium hydroxide, ammonium hydroxide, lithium hydroxide, potassium hydroxide, sodium carbonate, ammonium carbonate, lithium carbonate and mixtures thereof.

14. The process defined in claim 12 wherein the petroleum fractions of step (a) contain from about 10 to about 80 percent aromatics.

15. A process for producing a petroleum sulfonate comprising:
(a) separately sulfonating a least four different petroleum oil fractions from a single crude feed boiling substantially above 700° F. selected from the group consisting of:
(1) a first fraction comprised of components at least 90 percent by volume of which boil above 700°

F. and 50 percent by volume boil within the range of 720° F. to 820° F.;

(2) a second fraction comprised of components at least 90 percent by volume of which boil above 700° F. and 50 percent by volume boil within the range of 770° F. to 890° F.;

(3) a third fraction comprised of components at least 90 percent by volume of which boil above about 700° F. and 50 percent by volume boil in the range of 880° F. to 1000° F.;

(4) a fourth fraction obtained from a deasphalting unit comprised of components at least 90 percent by volume of which boil above about 700° F. and 30 percent by volume boil in the range of 1000° F to 1120° F.;

(b) neutralizing the sulfonated fractions obtained from step (a) by reaction with a neutralizing agent so as to produce sulfonates in each of the fractions;

(c) blending the sulfonated fractions obtained from step (b) in a ratio between 0:1:1:0 and 1:10:10:1 for the first, second, third, and fourth fractions, respectively, to produce a product sulfonate blend.

16. The process defined in claim 5 wherein the sulfonate produced in step (a) from said fraction defined in claim 5 has a sulfonate requirement in microemulsion below about 12 grams per 100 milliliters of microemulsion at optional salinity below about 7.

17. The process defined in claim 6 wherein the sulfonate produced in step (a) from said fraction defined in claim 6 has a sulfonate requirement in microemulsion below about 8 grams per 100 milliliters of microemulsion at optional salinity below about 4.

18. The process defined in claim 1 wherein said product petroleum sulfonate blend obtained in step (c) has at least 40 percent of the sulfonates being monosulfonates.

19. The process defined in claim 2 wherein said product petroleum sulfonate blend obtained in step (c) has at least 40 percent of the sulfonates being monosulfonates.

20. The process defined in claim 11 wherein said product sulfonate blend is produced having an average molecular weight below 500 with at least 40 percent of the sulfonates being monosulfonates.

* * * * *

UNITED STATES PATENT AND TRADEMARK OFFICE
CERTIFICATE OF CORRECTION

PATENT NO. : 4,847,018

DATED : July 11, 1989

INVENTOR(S) : Koepke et al.

It is certified that error appears in the above-identified patent and that said Letters Patent is hereby corrected as shown below:

Claim 7, column 17, line 26, after "above" insert -- about --.

Signed and Sealed this

Third Day of August, 1993

Attest:

MICHAEL K. KIRK

*Attesting Officer*     *Acting Commissioner of Patents and Trademarks*